United States Patent [19]

Brunelle et al.

[11] Patent Number: 5,132,423
[45] Date of Patent: Jul. 21, 1992

[54] METHOD FOR CONDUCTING ORGANIC REACTIONS USING GUANIDINIUM SALT AS PHASE TRANSFER CATALYST

[75] Inventors: Daniel J. Brunelle, Scotia; Deborah A. Haitko, Schenectady; James P. Barren, Scotia; Sunita Singh, Schenectady, all of N.Y.

[73] Assignee: General Electric Company, Schenectady, N.Y.

[21] Appl. No.: 668,560

[22] Filed: Mar. 13, 1991

Related U.S. Application Data

[63] Continuation-in-part of Ser. No. 474,869, Feb. 5, 1990, abandoned, and a continuation-in-part of Ser. No. 626,150, Dec. 12, 1990, abandoned.

[51] Int. Cl.⁵ .............. C07D 209/48; C07C 29/58; C07C 321/28; C07C 279/02
[52] U.S. Cl. .................................. 544/162; 546/231; 548/455; 548/473; 548/566; 558/411; 558/423; 504/241; 568/28; 568/29; 568/33; 568/41; 568/42; 568/44; 568/38; 568/585; 568/635
[58] Field of Search ............ 568/28, 41, 44, 38, 568/635, 29, 33, 42, 585; 558/423, 411; 548/473, 455, 566; 544/162; 546/231; 564/241

[56] References Cited

U.S. PATENT DOCUMENTS

| | | | |
|---|---|---|---|
| 4,554,357 | 11/1985 | Verbicky et al. | 548/473 |
| 4,273,712 | 6/1981 | Williams | 548/461 |
| 4,460,778 | 7/1984 | Brunelle et al. | 596/304 |
| 4,513,141 | 4/1985 | Brunelle et al. | 548/455 |
| 4,578,470 | 3/1986 | Webb | 548/374 |
| 4,681,949 | 7/1987 | Brunelle | 548/461 |

OTHER PUBLICATIONS

Denarie, et al. Tetrahedron Letters vol. 28(47) 5823–5826, 1987.
Jones Aldrichemica Acta vol. 9(3) 1976 pp. 35–45.
Wlostoski, et al. Chemical Abstracts vol. 113, 1990, Abstract 58127q.

Primary Examiner—Robert T. Bond
Assistant Examiner—E. C. Ward
Attorney, Agent, or Firm—William H. Pittman; James C. Davis, Jr.

[57] ABSTRACT

Reactions between a solid polar and a non-polar compound, especially nucleophilic aromatic substitution reactions between an alkali metal salt of a hydroxyaromatic compound or thio analog thereof and an activated halo- or nitro-substituted aromatic compound, are conducted in a non-polar organic solvent such as toluene or xylene, in the presence of a hexaalkylguanidinium or $\alpha,\omega$-bis(pentaalkylguanidinium)alkane salt, or a corresponding heterocyclic salt, as a phase transfer catalyst. The method is particularly useful for the preparation of bisimides from bisphenol A or 4,4'-biphenol salts and 4-nitro- or 4-halophthalimides.

21 Claims, No Drawings

METHOD FOR CONDUCTING ORGANIC REACTIONS USING GUANIDINIUM SALT AS PHASE TRANSFER CATALYST

This application is a continuation-in-part of copending applications Ser. Nos. 07/474,869 and 07/626,150 both now abandoned.

This invention relates to the preparation of organic compounds by the reaction of polar with non-polar compounds, and more particularly to a method of preparation thereof which employs improved phase transfer catalysts.

Various methods are known for conducting reactions between highly polar reagents, such as alkali metal salts of hydroxyaromatic compounds or thio analogs thereof, and substantially non-polar reagents such as activated halo- or nitro-substituted aromatic compounds. Typical nucleophilic aromatic substitution reactions of this type result in replacement of the halo or nitro group with an aryloxy or arylthio group.

Such nucleophilic aromatic substitution reactions are particularly useful commercially for the preparation of aromatic ether bisimides such as those of 2,2-bis[4-(dicarboxyphenoxy)phenyl]propane bisimides and 4,4'-bis(-dicarboxyphenoxy)biphenyl bisimides. These bisimides may be prepared by the reaction of salts of bisphenol A and of 4,4'-biphenol with N-alkylnitro- or N-alkylhalophthalimides. They may be converted to dianhydrides, which in turn undergo reaction with diamines to produce polyetherimides. Certain bisimides also react directly with diamines to produce polyetherimides, as disclosed, for example, in U.S. Pat. No. 4,578,470. The analogous monoimides are similarly useful as endcapping or chain-stopping agents for polyimides.

In most cases, it was formerly necessary to conduct reactions of this type (including nucleophilic displacement reactions) in polar aprotic solvents, since the alkali metal salts are typically insoluble in non-polar solvents. Commercial preparation of aromatic ethers was therefore inhibited by various disadvantages of polar aprotic solvents, including high cost, difficulty of recycling and toxicity.

More recently, it has been possible to conduct the reaction in non-polar solvents with the employment of a phase transfer catalyst, facilitating incorporation of the salt of the hydroxyaromatic compound in the organic phase. Many types of phase transfer catalysts are known, including quaternary ammonium and phosphonium salts as disclosed in U.S. Pat. No. 4,273,712. More specifically, there have been used various bis-quaternary ammonium or phosphonium salts as disclosed in U.S. Pat. No. 4,554,357, and aminopyridinium salts as disclosed in U.S. Pat. Nos. 4,460,778, 4,513,141 and 4,681,949.

Despite the improvements afforded by the use of phase transfer catalysts as described in the above-identified patents, several problems remain. In the first place, the reaction is often quite slow when those catalysts are employed. In the second place, yields are often very low, particularly when halophthalimides are employed. In the third place, decomposition of the phase transfer catalyst usually occurs during the reaction, necessitating frequent replacement thereof and resulting in the formation of by-products which cause discoloration of the product and may lead to undesirable side reactions.

The low yields encountered with the use of halophthalimides are illustrated by the reaction of 4-chloro-N-methylphthalimide with bisphenol A disodium salt in the presence of 1,6-bis(tri-n-butylammonium)hexane dibromide, which yields 2,2-bis[4-(3,4-dicarboxyphenoxy)phenyl]propane bis-N-methylimide in only 5% yield after 2-½ hours. By contrast, the yield is greater than 95% after 30 minutes using the 4-nitro compound.

Catalyst decomposition is particularly noticeable in the preparation of 4,4'-bis(dicarboxyphenoxy)biphenyl bisimides by the reaction of nitrophthalimides with 4,4'-biphenol salts, using a bis(trialkylammonium)alkane dihalide as catalyst. When the reaction is conducted in refluxing toluene as solvent, high yields are obtained. However, in xylene (which has a higher boiling point) the yield is much lower if the catalyst is exposed to reflux temperatures prior to initiation of the reaction, in the course of drying the nitrophthalimide. Yields increase somewhat if the catalyst is not introduced until after drying, but are still lower than desired.

The present invention is based on the discovery that certain guanidinium and α,ω-bis(pentaalkylguanidinium)alkane salts may be employed as phase transfer catalysts in reactions between polar and non-polar compounds. The use of these salts frequently increases the reaction rate and yield substantially as compared with the use of previously known phase transfer catalysts in comparable amounts. In addition, said guanidinium salts have a high degree of thermal stability and thus do not undergo substantial decomposition during the displacement reaction. This means less color formation in the product and the potential for recycling of catalyst, decreasing the cost of the process.

Accordingly, the invention is a method for effecting reaction in a non-polar organic solvent between a highly polar compound which is insoluble in said solvent and a substantially non-polar compound which is soluble therein, which comprises conducting said reaction in the presence of at least one guanidinium or α,ω-bis(pentaalkylguanidinium)alkane salt as a phase transfer catalyst.

The present invention is capable of use in connection with an extremely broad spectrum of reactions between organic chemicals. In general, it may advantageously be employed in any situation where reaction is to be effected between one reagent which is highly polar and insoluble in the non-polar liquid to be used as solvent, and another which is substantially non-polar and is soluble therein. More particularly, it is applicable to reagents employed in nucleophilic aromatic substitution reactions, and still more particularly to the reaction between at least one alkali metal salt of a hydroxyaromatic compound or thio analog thereof and at least one activated halo- or nitro-substituted aromatic compound. For the sake of convenience, these reagents will be the principal ones hereinafter and they will be specifically identified as "phenol salt" and "activated aromatic compound", respectively.

The phenol salts are generally compounds of the formula $$R^1(ZM)_a$$

wherein $R^1$ is an aromatic radical containing about 6–30 carbon atoms, M is an alkali metal, Z is oxygen or sulfur and a is 1 or 2. The $R^1$ radical may be a hydrocarbon radical or may contain other atoms such as oxygen or sulfur. Illustrative monovalent radicals (i.e., those derived from compounds in which a is 1) include phenyl, m-tolyl, p-tolyl, 1-naphthyl, 2-naphthyl, p-chlorophenyl and 4-bromo-1-naphthyl.

Most often, $R^1$ is a divalent aromatic radical; i.e., a is 2. Illustrative dihydroxyaromatic compounds are resorcinol, hydroquinone, 4,4'-dihydroxybiphenyl, 4,4'-dihydroxy-3,3',5,5'-tetramethylbisphenyl, bis(4-hydroxyphenyl)methane, 3-hydroxyphenyl-4-hydroxyphenylmethane, 2,2-bis(2-hydroxyphenyl)propane, 2,2-bis(4-hydroxyphenyl)propane (hereinafter "bisphenol A"), 2-(3-hydroxyphenyl)-2-(4-hydroxyphenyl)propane, 1,1-bis(4hydroxyphenyl)ethane, 2,2-bis(4-hydroxyphenyl)pentane, 1,1-bis(4-hydroxyphenyl)ethylene, 4,4'-dihydroxybenzophenone, bis(4-hydroxyphenyl)ether, bis(4-hydroxyphenyl) sulfide, bis(4-hydroxyphenyl) sulfoxide, bis(4-hydroxyphenyl) sulfone and 3-hydroxyphenyl-4-hydroxyphenyl sulfone.

The preferred $R^1$ radicals are usually

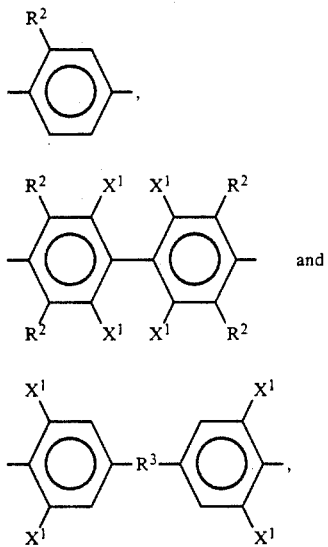

and wherein each $R^2$ is independently hydrogen or methyl, $R^3$ is a straight-chain or branched alkylene radical containing 1-5 carbon atoms and each $X^1$ is independently hydrogen or halogen (usually chlorine or bromine). Mixtures of the foregoing formulas are also contemplated. Especially desirable are the bisphenol A salts, having formula IV in which $R^3$ is isopropylidene and each $X^1$ is hydrogen.

The alkali metal in the phenol salt may be any of the known alkali metals. Sodium and potassium are usually preferred by reason of availability and low cost, with sodium being especially preferred. The Z value may be oxygen or sulfur and is usually oxygen.

By "activated aromatic compound" is meant a compound having an electron-deficient aromatic ring, generally achieved by the presence of one or more electron-withdrawing substituents. Illustrative substituents of this type are halo, nitro, acyl, cyano, carboxy, carbalkoxy, aldehydo, sulfone and perfluoroalkyl, as well as heterocyclic aromatic substituents such as pyridyl.

Most often, the activated aromatic compound is a substituted imide having the formula

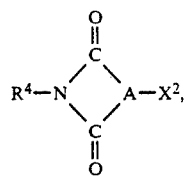

wherein A is an aromatic radical, $R^4$ is hydrogen or an unsubstituted or substituted hydrocarbon radical containing about 1-13 carbon atoms and $X^2$ is halo or nitro. The A radical generally contains about 6-30 carbon atoms. The imide is generally derived from an o-dicarboxylic acid such as phthalic acid or 2,3-naphthalenedicarboxylic acid; however, derivatives of acids such as 1,8-naphthalenedicarboxylic acid are also suitable. Most preferably, the imide is a phthalimide.

The $R^4$ value is preferably an alkyl and especially a lower alkyl radical (i.e., one containing up to 7 carbon atoms). Most preferably, $R^4$ is methyl or n-butyl.

According to the invention, the reaction between the phenol salt and the substituted aromatic compound is conducted in a non-polar organic solvent. Suitable solvents include benzene, toluene, xylene, chlorobenzene, o-dichlorobenzene, chlorotoluene, dichlorotoluene and octane. Aromatic solvents are preferred, with aromatic hydrocarbon solvents and especially toluene being particularly preferred.

An essential aspect of the invention is the employment of at least one guanidinium or α,ω-bis(pentaalkylguanidinium)alkane salt as a phase transfer catalyst. For the sake of brevity, both types of salts are hereinafter sometimes designated "guanidinium salt".

Suitable guanidinium salts are represented by the formula

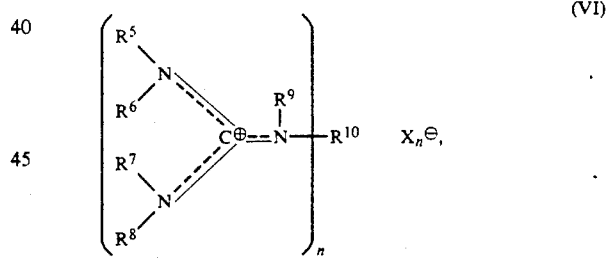

wherein each of $R^5$, $R^6$, $R^7$ and $R^8$ is a primary alkyl radical or at least one of the $R^5$-$R^6$ and $R^7$-$R^8$ combinations with the connecting nitrogen atom forms a heterocyclic radical, $R^9$ is a primary alkyl radical, $R^{10}$ is a primary alkyl or bis(primary alkylene) radical, X is an anion and n is 1 or 2.

The alkyl radicals suitable as $R^{5-9}$ are primary alkyl radicals, generally containing about 1-12 and preferably about 2-6 carbon atoms. Alternatively, any combination of $R^{5-8}$ and the corresponding nitrogen atom(s) may form a heterocyclic radical such as piperidino, pyrrolo or morpholino. $R^{10}$ is usually an alkyl radical of the same structure or a $C_{2-12}$ alkylene radical in which the terminal carbons are primary; most preferably, it is $C_{2-6}$ alkyl or $C_{4-8}$ straight chain alkylene. α,ω-Bis(pentaalkylguanidinium)alkane salts are disclosed and claimed in copending, commonly owned application Ser. No. 07/719,458.

The X value may be any anion and is preferably an anion of a strong acid; examples are chloride, bromide and methanesulfonate. Chloride and bromide ions are usually preferred. The value of n will be 1 or 2 depending on whether $R^{10}$ is alkyl or alkylene.

As indicated by the dotted bonds in formula VI, the positive charge in the guanidinium salt is delocalized over one carbon and three nitrogen atoms. This is believed to contribute to the salt's stability under the conditions encountered according to the invention, including relatively high temperatures. As a result, decomposition of the guanidinium salt does not occur or occurs only to a very minor extent. The results include suppression of by-product formation and potential for continued use via recycle.

The guanidinium salts suitable for use as phase transfer catalysts according to the invention may be prepared by the reaction of a tetraalkylurea or heterocyclic analog thereof with phosgene or phosphorus oxychloride, or by the reaction of a corresponding thiourea with an N,N-dialkylcarbamoyl halide, to yield a chloroformamidinium salt, frequently referred to as a "Vilsmeier salt", followed by reaction of said salt with a dialkylamine. Reference is made to Kantlehner et al., *Liebigs Ann. Chem.*, 1984, 108–126, and Pruszynski, *Can. J. Chem.*, 65, 626–629 (1987), which are incorporated by reference herein. α,ω-Bis(pentaalkylguanidinium)alkane salts may be similarly prepared by reaction of the chloroformamidinium salt with a monoalkylamine, followed by reaction of the resulting pentaalkylguanidinium salt with an alkylene dihalide.

The preparation of guanidinium salts is illustrated by the following examples.

EXAMPLE 1

A 3-liter, 5-necked flask fitted with a mechanical stirrer, condenser, phosgene inlet tube, pH meter and addition port was charged with 182.85 grams (2.5 moles) of diethylamine, one liter of methylene chloride and 200 ml. of water. Phosgene (99 grams, 1 mole) was passed into the mixture under nitrogen, with stirring, at the rate of 3 grams per minute, with addition of aqueous sodium hydroxide solution to maintain the pH in the range of 10–12. A vigorous exothermic reaction took place during phosgene addition, causing refluxing of the methylene chloride. After phosgene addition was complete, the mixture was maintained at a pH of 12 while refluxing was continued for 2 hours. The methylene chloride phase was separated, washed with water and vacuum stripped to yield the desired crude tetraethylurea in quantitative yield based on phosgene.

To a solution of 172.3 grams (1 mole) of tetraethylurea in 100 ml. of dry toluene was added under nitrogen, with stirring, 170 grams (1.05 moles) of phosphorus oxychloride. The mixture was stirred and warmed at 60° C. for 2 hours under nitrogen, whereupon the Vilsmeier salt separated as a second phase. Periodic analysis by nuclear magnetic resonance indicated when the reaction was complete. At that point, the mixture was cooled to 0° C. and diluted with 500 ml. of dry methylene chloride. There was then added, under nitrogen, 182 grams (2.5 moles) of diethylamine, with stirring at 0° C. An exothermic reaction took place, and when it was complete the mixture was warmed to room temperature and analyzed by proton nuclear magnetic resonance. Additional diethylamine was added until no further Vilsmeier salt was present in the mixture, after which 400 ml. of 35% aqueous sodium hydroxide was added carefully and the mixture was extracted with methylene chloride. The organic phase was washed with saturated sodium chloride solution, dried and evaporated to afford the crude product as a yellow oil which crystallized upon addition of ethyl acetate. Upon filtration of the ethyl acetate slurry, the desired hexaethylguanidinium chloride was obtained in 87% yield. It could be recrystallized from a mixture of equal volumes of heptane and ethyl acetate, with enough chloroform added to effect solution when hot.

EXAMPLE 2

Hexaethylguanidinium chloride, obtained according to Example 1, was dissolved in methylene chloride and the solution was washed three times with saturated aqueous sodium bromide solution. Upon workup as described in Example 1, the desired hexaethylguanidinium bromide was obtained; it had a melting point of 174°–175° C.

EXAMPLE 3

The procedure of Examples 1–2 was repeated, substituting tetra-n-butylurea and di-n-butylamine for the tetraethylurea and diethylamine, respectively. The product was the desired hexa-n-butylguanidinium bromide.

EXAMPLE 4

A mixture of 56.9 grams (200 mmol.) of tetra-n-butylurea, 32.2 grams (210 mmol.) of phosphorus oxychloride and 75 ml. of acetonitrile was heated at 75° C. in a nitrogen atmosphere for one hour. The mixture was then cooled to 0° C. and 33.6 grams (460 mmol.) of n-butylamine was added over 15 minutes with stirring, whereupon a soft, fluffy precipitate formed. The mixture was warmed to 60° C. for one hour and again cooled to 0° C., quenched with 50 ml. of 25% (by weight) aqueous sodium hydroxide solution and extracted with ether. The ether extracts were dried over magnesium sulfate, filtered and stripped to give a pale yellow oil which, upon distillation, yielded 56.32 grams (83% of theoretical) of penta-n-butylguanidine.

A mixture of 16.98 grams (50 mmol) of penta-n-butylguanidine, 6.0995 grams (25 mmol.) of 1,6-dibromohexane and 50 ml. of acetonitrile was heated under reflux in a nitrogen atmosphere for 16 hours, after which proton nuclear magnetic spectroscopy showed the absence of carbon-bromine absorption. Upon vacuum stripping, a pale yellow oil was obtained which crystallized to a white solid upon standing. Upon recrystallization from a mixture of hexane and ethyl acetate, the desired 1,6-bis(N,N',N',N'',N''-penta-n-butylguanidinium)hexane dibromide, which melted at 100°–102° C.; its structure was confirmed by proton and carbon-13 nuclear magnetic resonance and Fourier transform infrared spectroscopy.

EXAMPLE 5

The procedure of Example 4 was repeated, substituting tetraethylurea on an equimolar basis for the tetra-n-butylurea and employing a mixture of 25 mmol. each of n-butylamine and triethylamine, the latter serving as a hydrogen chloride acceptor. The product was the desired 1,6-bis(N-n-butyl-N',N', N'',N'''-tetraethylguanidinium)hexane dibromide.

EXAMPLE 6

Phosgene was passed for 17 minutes, at the rate of 3 grams per minute, through a mixture of 84 grams (1 mole) of piperidine, 500 ml. of methylene chloride and 100 ml. of water. The pH was maintained in the range of 8-11 by the addition of 50% aqueous sodium hydroxide solution during the latter portion of the phosgene passage. An exothermic reaction occurred which caused refluxing of the mixture. After phosgenation was complete, additional base was added until the pH remained constant at 11 for 5 minutes, after which 200 ml. of water was added and the organic layer was removed, washed twice with aqueous hydrochloric acid solution and filtered. Upon vacuum stripping, the desired bis(pentamethylene)urea was obtained in 96% yield. Its structure was confirmed by proton nuclear magnetic resonance spectroscopy.

A solution of 9.8 grams (50 mmol.) of bis(pentamethylene)urea in 50 ml. of toluene was stirred in an argon atmosphere and 5 ml. (55 mmol.) of phosphorus oxychloride was added. The mixture was warmed at 75° C. for 1 hour, whereupon two phases formed. Proton nuclear magnetic resonance spectroscopy showed that conversion to the Vilsmeier salt was complete.

The mixture was cooled to 0° C. and 12 ml. (120 mmol.) of piperidine was added dropwise. The mixture was then warmed to 50° C. and maintained at that temperature for 15 minutes. It was again cooled to 0° C. and 25 ml. of 10 M aqueous sodium hydroxide solution was added over 5 minutes. The mixture was diluted with 100 ml. of water and 100 ml. of hexane was added. The organic layer was removed, washed with water and discarded.

To the combined aqueous layer and washings was added 50 ml. of saturated sodium bromide solution. The mixture was extracted three times with 50 ml. portions of methylene chloride, and the extracts were washed with sodium bromide solution, filtered and evaporated. There was obtained a solid product which was washed with ethyl acetate, yielding white crystals which were removed by filtration and dried. The desired tris(pentamethylene)guanidinium bromide was obtained in 87% yield; its melting point was 186°-187.5° C. The molecualr structure was confirmed by proton nuclear magnetic resonance spectroscopy.

EXAMPLE 7-12

Following the procedure of Example 6, heterocyclic products were prepared in accordance with Table I.

TABLE I

| Example | Urea | Amine | Product Yield, % | Melting point, °C. |
|---|---|---|---|---|
| 7 | Bis(pentamethylene) | Pyrrolidine | 94 | 146-148 |
| 8 | Bis(pentamethylene) | Diethylamine | 93 | Oil |
| 9 | Bis(pentamethylene) | Morpholine | 42 | 165-167 |
| 10 | Bis(tetramethylene) | Pyrrolidine | 96 | 213-215 |
| 11 | Bis(tetramethylene) | Diethylamine | 92 | Oil |
| 12 | Bis(tetramethylene) | Morpholine | 22 | 211-214 |

In the method of this invention, the reaction mixture containing the phenol salt, activated aromatic compound, guanidinium salt and solvent is normally heated at a temperature in the range of about 100°-200° C., preferably about 125°-175° C. It is preferred to use stoichiometric amounts of the phenol salt and activated aromatic compound, but under appropriate conditions an excess of one reagent or the other (especially the phenol salt), generally not more than about 25%, may be employed. An internal standard may be incorporated in the reaction mixture for analytical purposes. The proportion of guanidinium salt is a catalytically effective proportion, most often about 0.5-5.0 mole percent based on activated aromatic compound in the case of guanidinium salts and about 0.25-2.5 mole percent in the case of $\alpha,\omega$-bis(guanidinium)alkane salts. In the case of a compound containing both halo and nitro substituents, the halo substituent is normally displaced.

When isolation of the product is required, it may be achieved by conventional methods. These typically involve washing with an aqueous alkaline solution followed by drying of the organic phase and solvent stripping.

For the preparation of 2,2-bis[4-(dicarboxyphenoxy)phenyl]propane bisimides, the preferred guanidinium salts are those in which the n is 1 and $R^{5-10}$ are alkyl groups containing up to 3 carbon atoms, with the hexaethyl compound being most preferred. On the other hand, highest yields of 4,4'-bis(4-dicarboxyphenoxy)biphenols are generally obtained by the use of salts in which the alkyl groups contain 4-6 carbon atoms, especially the hexa-n-butyl compound, or the corresponding heterocyclic salts and especially the piperidinium salt. The reasons for this phenomenon are not presently known. The piperidinium salts have particularly high thermal stability as shown by thermogravimetric analysis; %5 weight loss occurs at 321° C., as compared with 277° C. for the hexaethyl compound. Thus, their use may be preferred when the reaction mixture must undergo long exposure to high temperature conditions.

The method of this invention is illustrated by the following examples. All percentages are by weight. "Chromatographic yield" is yield as determined by high pressure liquid chromatography.

EXAMPLES 13-20

Sodium p-cresoxide was prepared by the reaction of p-cresol with sodium hydroxide in aqueous solution, followed by addition of toluene and removal of water by azeotropic distillation. A mixture of 780 mg. (6 mmol.) of sodium p-cresoxide and 800 mg. (5 mmol.) of p-chloronitrobenzene was prepared in an anhydrous nitrogen atmosphere, and there were added 22 ml. of solvent and a small amount of tetracosane as an internal standard. The solvent included at least 2 ml. of toluene, which was removed by distillation in a nitrogen atmosphere, with stirring, to effect azeotropic drying of the reactants. Guanidinium salt was then added in the appropriate amount, as a stock solution in o-dichlorobenzene, and heating and stirring were continued with portions of the reaction mixture being periodically removed, quenched with acetic acid, diluted with methylene chloride and analyzed by vapor phase chromatography.

The reaction parameters and yields of 4-cresyl-4'-nitrophenyl ether obtained, are listed in Table II. Solvents are identified as follows:

Tol - toluene;
PhCl - chlorobenzene;
DCB - o-dichlorobenzene.

TABLE II

| | Example | | | | | | | |
|---|---|---|---|---|---|---|---|---|
| | 13 | 14 | 15 | 16 | 17 | 18 | 19 | 20 |
| Solvent | PhCl | DCB | DCB | DCB | PhCl | Tol | PhCl | PhCl |
| Guanidinium salt (formula VI): | | | | | | | | |
| $R^{5-8}$ | $C_2H_5$ | $C_2H_5$ | $C_2H_5$ | $C_2H_5$ | $C_4H_9$ | $CH_3$ | $CH_3$ | $C_4H_9$ |
| $R^9$ | $C_2H_5$ | $C_2H_5$ | $C_2H_5$ | $C_2H_5$ | $C_4H_9$ | $C_6H_{13}$ | $C_6H_{13}$ | $C_4H_9$ |
| $R^{10}$ | $C_2H_5$ | $C_2H_5$ | $C_2H_5$ | $C_2H_5$ | $C_4H_9$ | $CH_3$ | $CH_3$ | $C_6H_{12}$ |
| X | Cl | Cl | Br | Br | Br | Br | Br | Br |
| n | 1 | 1 | 1 | 1 | 1 | 1 | 1 | 2 |
| Mole %* | 1.0 | 0.5 | 1.0 | 0.25 | 1.0 | 1.0 | 1.0 | 0.25 |
| Temperature, °C. | 130 | 150 | 150 | 150 | 130 | 110 | 130 | 140 |
| Chromatographic yield, %: | | | | | | | | |
| 15 min. | — | — | 97 | — | — | — | — | — |
| 30 min. | 99 | — | — | 65 | 92 | — | 88 | 93 |
| 1 hr. | — | — | — | 72 | — | — | 100 | — |
| 2 hrs. | — | 98 | — | — | — | 69 | — | — |
| 4 hrs. | — | — | — | 87 | — | — | — | — |
| 20 hrs. | — | — | — | — | — | 99 | — | — |

*Based on p-chloronitrobenzene.

EXAMPLES 21-27

Following substantially the procedure of Examples 13-20, various reactions between 4-substituted chlorobenzenes and sodium p-cresylate or p-thiocresylate, using hexaethylguanidinium bromide as the phase transfer catalyst. The relative parameters and yields are given in Table III.

TABLE III

| | Example | | | | | | |
|---|---|---|---|---|---|---|---|
| | 21 | 22 | 23 | 24 | 25 | 26 | 27 |
| Alkali metal salt: Z (formula I) | S | O | O | S | S | S | S |
| Activated aromatic compound: Substituent | $NO_2$ | CN | $SO_2C_6H_5$ | CN | $SO_2C_6H_5$ | $COC_6H_5$ | CHO |
| Catalyst mole % | 1 | 5 | 5 | 1 | 1 | 1 | 1 |
| Temperature, °C. | 130 | 180 | 130 | 180 | 130 | 130 | 130 |
| Time, min. | 15 | 480 | 60 | 120 | 120 | 180 | 120 |
| Solvent | PhCl | DCB | PhCl | DCB | PhCl | PhCl | PhCl |
| Chromatographic yield, % | 94 | 72 | 97 | 96 | 95 | 88 | 87 |

EXAMPLES 28-29

In catalyst stability tests, 308 mg. (1 mmol.) of hexaethylguanidinium bromide was heated under reflux, with stirring, with 260 mg. (2 mmol.) of sodium p-cresoxide in refluxing chlorobenzene (Example 28) and refluxing o-dichlorobenzene (Example 29) for 2 hours, in a nitrogen atmosphere. The mixtures were cooled and extracted with 2 M aqueous sodium hydroxide, and the aqueous extracts were washed with petroleum ether and extracted with methylene chloride. Any remaining p-cresol salt was removed by washing with 10% aqueous potassium hydroxide solution, and the methylene chloride solutions were dried over magnesium sulfate and vacuum stripped. The amount of hexaethylguanidinium bromide recovered was in the range of 84-88%.

EXAMPLE 30

A 50-ml. round-bottomed two-necked flask fitted with a reflux condenser, a magnetic stir bar and a nitrogen inlet was charged with 3 grams (11 mmol.) of the disodium salt of bisphenol A, 4.54 grams (22 mmol.) of 4-nitro-N-methylphthalimide, 0.5 gram of 1,3,5-triphenylbenzene as an internal standard, 685 mg. (0.26 mmol.) of hexaethylguanidinium chloride and 17.1 grams of toluene. The flask was purged with nitrogen and heated under reflux for 45 minutes; samples were periodically taken, quenched with a mixture of urea, acetonitrile, methanol and acetic acid and analyzed by high pressure liquid chromatography. At the end of the reaction period, the mixture was diluted with toluene to 22% solids and 6 ml. of 0.8% aqueous sodium hydroxide solution was added at 80° C. The mixture was stirred at this temperature for 15 minutes, after which the organic layer was removed and washed twice more with aqueous base. The toluene was vacuum stripped to yield the desired 2,2-bis[4-(3,4dicarboxyphenoxy)phenyl]propane bis-N-methylimide in 94.7% yield.

A solution of exactly 500 mg. of the bisimide in exactly 10 ml. of chromatographic grade methylene chloride was stirred until all the bisimide had dissolved. The yellowness index of the solution was then measured in a Gardner Instruments colorimeter, and was found to be 5.0.

A control reaction was conducted by an identical procedure except that the hexaethylguanidinium chloride was replaced by an equivalent amount of 1,6-bis(tri-n-butylammonium) dibromide (i.e., 0.13 mmol., since the equivalent weight of this compound is half its molecular weight). The product was isolated in 92% yield and had a yellowness index value of 22.2.

EXAMPLES 31-32

The procedure of Example 30 was repeated, employing half the quantities of each reagent and replacing the hexaethylguanidinium chloride with an equivalent amount of hexaethylguanidinium bromide (Example 31) and hexa-n-butylguanidinium bromide (Example 32).

The isolated yields and yellowness indices of the products were as follows:
Example 31 - 91%; 5.6.
Example 32 - 88%; 8.3.

EXAMPLE 33

A dry 50-ml. flask fitted with a magnetic stir bar was purged with argon and charged with 2.72 grams (10 mmol.) of bisphenol A disodium salt, 4.12 grams (22 mmol.) of 4-nitro-N-methylphthalimide, 0.22 mmol. of 1,6-bishexylene(penta-n-butylguanidinium) dibromide and 20 ml. of toluene. The mixture was heated with stirring as 2 ml. of toluene was removed by distillation along with any water present (as an azeotrope), after which heating under reflux was continued. Analysis by high pressure liquid chromatography indicated a yield after 15 minutes of 94% of the theoretical amount of 2,2-bis[4-(3,4dicarboxyphenoxy)phenyl]propane bis-N-methylimide.

EXAMPLE 34

The reaction vessel was a 100-ml. round bottomed flask fitted with a mechanical stirrer and a Dean-Stark trap bearing a reflux condenser and a nitrogen inlet and linked with the reaction vessel by a tube filled with calcium hydride and plugged with cheesecloth below and glass wool above the calcium hydride. The vessel was charged with 8 grams (32.2 mmol.) of 4-nitro-N-butylphthalimide, 495 mg. (0.806 mmol.) of hexa-n-butylguanidinium bromide, 400 mg. of biphenyl as an internal standard and 16.4 ml. of toluene. The mixture was purged with nitrogen for 5 minutes; heated under reflux for 50 minutes in a nitrogen atmosphere, with stirring; and cooled, after which 3.71 grams (16.1 mmol.) of dry 4,4'-biphenol disodium salt was added. Heating under reflux in a nitrogen atmosphere was resumed and the reaction was monitored at 30-minute intervals by high pressure liquid chromatography after the aliquots being sampled had been diluted with chloroform, treated with dimethylacetamide and filtered.

After 2.5 hours of refluxing, the mixture was cooled to 80° C. and washed three times with 15 ml. of 0.8% aqueous sodium hydroxide which had been preheated to 85° C. In each washing step, the mixture was stirred for 15 minutes before removal of the aqueous layer. The toluene was removed by vacuum stripping, to yield the desired 4,4'-bis(3,4-dicarboxyphenoxy)biphenyl bis-N-(n-butyl)imide. The chromatographic and isolated yields were 98.7% and 97.7%, respectively.

In a control similar to that described for Example 30, the chromatographic and isolated yields were 96% and 92%, respectively.

EXAMPLE 35

The procedure of Example 34 was repeated, substituting xylene for the toluene and thus providing a substantially higher reaction temperature. The chromatographic and isolated yields were 99% and 96.3%, respectively.

In the control, the chromatographic yield was only 55.1% and the isolated yield was 57.5%. When the procedure was modified by adding the catalyst with the biphenol disodium salt, rather than with the 4-nitro-N-butylphthalimide, the chromatographic yield was 86.3% and the isolated yield was 86.0%.

EXAMPLE 36

A 50-ml. round-bottomed flask fitted with a magnetic stir bar, condenser and nitrogen inlet was charged with 1.458 grams (5.35 mmol.) of bisphenol A disodium salt, 3.021 grams (10.7 mmol.) of 4-bromo-N-n-butylphthalimide, 169 mg. (0.53 mmol.) of hexaethylguanidinium bromide, 206.3 mg. of 1,3,5-triphenylbenzene as an internal standard and 3.2 ml. of o-dichlorobenzene. The mixture was heated at 170° C., with stirring, and periodically sampled. After 30 minutes, analysis of a sample by high pressure liquid chromatography showed the formation of 2,2-[4-(3,4-dicarboxyphenoxy)phenyl]propane bis-N-n-butylimide in 95% yield. A control run under similar conditions but using 1,6-bis(tri-n-butylammonium)hexane dibromide gave a yield of only after 3 hours.

EXAMPLE 37

The procedure was similar to that of Example 36, except that the hexaethylguanidinium bromide was replaced with half the molar amount of 1,6-bis(penta-n-butylguanidinium)hexane dibromide. The yield was 93% after 30 minutes.

EXAMPLE 38

A reaction vessel similar to that of Example 36 was charged with 2.0123 grams (7.4 mmol.) of bisphenol A disodium salt, 2.8966 grams (14.8 mmol.) of 4-chloro-N-methylphthalimide, 121.8 mg. (0.4 mmol.) of hexaethylguanidinium bromide, 305.6 mg. of 1,3,5-triphenylbenzene and 4.6 ml. of toluene. The mixture was heated under reflux, with stirring, for 1-1/4 hours, after which 2,2-bis[4-(3,4-dicarboxyphenoxy)phenyl]propane bis-N-methylimide was detected in 93% yield by dilution with toluene, repeated washing with aqueous sodium hydroxide solution and high pressure liquid chromatography. A control run under identical conditions but using 1,6-bishexylene(penta-n-butylguanidinium) dibromide gave a yield of 35% after 1 hour, which was not improved upon additional heating.

What is claimed is:

1. A method for effecting reaction in a non-polar organic solvent between an alkali metal salt of a hydroxyaromatic compound or thio analog thereof and a substituted imide having the formula

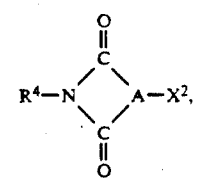

(V)

wherein A is an aromatic radical, $R^4$ is hydrogen or a hydrocarbon radical containing about 1-13 carbon atoms and $X^2$ is halo or nitro, which comprises conducting said reaction in the presence of at least one guanidinium or a, ω-bis(guanidinium)alkane salt of the formula

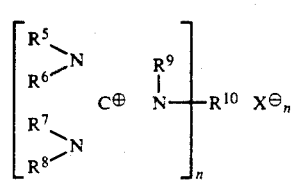

(VI)

as a phase transfer catalyst, wherein each of $R^5$, $R^6$, $R^7$ and $R^8$ is a primary alkyl radical or at least one of the $R^5$–$R^6$ and $R^7$–$R^8$ combinations with the connecting nitrogen atom forms a piperidino, pyrrolo or morpholino radical, $R^9$ is a primary alkyl radical, $R^{10}$ is a bis(primary alkylene) radical, X is an anion and n is 1 or 2.

2. A method according to claim 1 wherein the alkali metal salt has the formula $$R^1(ZM)_a \qquad (I)$$

wherein $R^1$ is an aromatic radical containing about 6–30 carbon atoms, M is sodium or potassium, Z is oxygen or sulfur and a is 1 or 2.

3. A method according to claim 2 wherein M is sodium and a is 2.

4. A method according to claim 3 wherein the solvent is toluene or xylene.

5. A method according to claim 4 wherein the substituted imide is a 4-nitro-, 4-bromo- or 4chlorophthalimide.

6. A method according to claim 5 wherein the alkali metal salt is the disodium salt of bisphenol A or of 4,4'-biphenol.

7. A method according to claim 6 wherein the reaction is conducted at a temperature in the range of about 100°–200° C.

8. A method according to claim 7 wherein stoichiometric amounts of the alkali metal salt and 4-nitrophthalimide are employed.

9. A method according to claim 6 wherein the guanidinium salt is a hexaalkylguanidinium salt and the proportion thereof is about 0.5–5.0 mole percent based on 4-nitrophthalimide.

10. A method according to claim 9 wherein the alkali metal salt is a bisphenol A salt.

11. A method according to claim 10 wherein $R^4$ is methyl.

12. A method according to claim 11 wherein the hexaalkylguanidinium salt is hexaethylguanidinium chloride.

13. A method according to claim 11 wherein the hexaalkylguanidinium salt is hexaethylguanidinium bromide.

14. A method according to claim 6 wherein the alkali metal salt is a 4,4'-biphenol salt.

15. A method according to claim 14 wherein $R^4$ is n-butyl.

16. A method according to claim 15 wherein the hexaalkylguanidinium salt is hexa-n-butylguanidinium chloride.

17. A method according to claim 15 wherein the hexaalkylguanidinium salt is hexa-n-butylguanidinium bromide.

18. A method according to claim 6 wherein the guanidinium salt is an $\alpha,\omega$-bis(pentaalkylguanidinium)alkane salt and the proportion thereof is about 0.25–2.5 mole percent based on 4-nitrophthalimide.

19. A method according to claim 18 wherein the alkali metal salt is a bisphenol A salt.

20. A method according to claim 19 wherein $R^4$ is methyl.

21. A method according to claim 20 wherein the $\alpha,\omega$-bis(pentaalkylguanidinium)alkane salt is 1,6-bis(penta-n-butylguanidinium)hexane dibromide.

* * * * *

UNITED STATES PATENT AND TRADEMARK OFFICE
CERTIFICATE OF CORRECTION

Page 1 of 2

PATENT NO. : 5,132,423
DATED : July 21, 1992
INVENTOR(S) : Daniel J. Brunelle, et. al.

It is certified that error appears in the above-indentified patent and that said Letters Patent is hereby corrected as shown below:

Column 4, lines 40-49, the formula should read

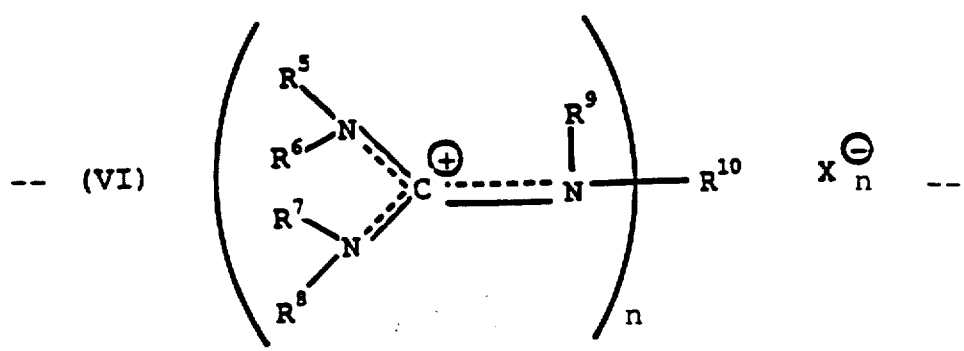

UNITED STATES PATENT AND TRADEMARK OFFICE
CERTIFICATE OF CORRECTION

PATENT NO. : 5,132,423

DATED : July 21, 1992

INVENTOR(S) : Daniel J. Brunelle et al.

It is certified that error appears in the above-identified patent and that said Letters Patent is hereby corrected as shown below:

Column 12, lines 61-70, the formula should read

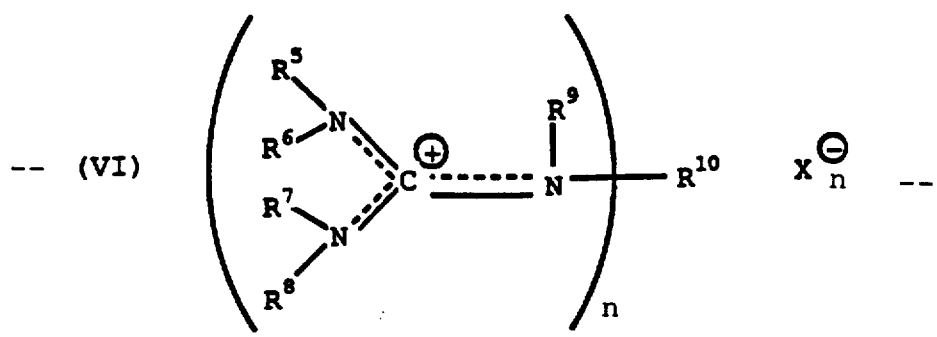

Signed and Sealed this

Nineteenth Day of October, 1993

Attest:

BRUCE LEHMAN

Attesting Officer      Commissioner of Patents and Trademarks